United States Patent
Zentgraf et al.

(10) Patent No.: US 6,214,541 B1
(45) Date of Patent: Apr. 10, 2001

(54) PROCESS FOR DETECTING SPECIFIC ANTIBODIES ACTING AGAINST HPV PROTEINS

(75) Inventors: Hanswalter Zentgraf, Heidelberg; Manfred Frey, Mannheim; Iris Velhagen, Schwetzingen; Regina Martens, Sandhausen; Wolfgang Meschede, Heidelberg; Michael Pawlita, Eschelbronn; Joris Braspenning, Schonbrunn; Masimo Tommasino, Bruchsal, all of (DE)

(73) Assignee: Deutsches Krebsforschungszentrum Stiftung Des Offentlichen Rechts, Heidelberg (DE)

( * ) Notice: Subject to any disclaimer, the term of this patent is extended or adjusted under 35 U.S.C. 154(b) by 0 days.

(21) Appl. No.: 08/981,870

(22) PCT Filed: Jul. 4, 1996

(86) PCT No.: PCT/DE96/01195

§ 371 Date: Mar. 9, 1998

§ 102(e) Date: Mar. 9, 1998

(87) PCT Pub. No.: WO97/02491

PCT Pub. Date: Jan. 23, 1997

(30) Foreign Application Priority Data

Jul. 4, 1995 (DE) ............................................. 195 24 346
Jul. 4, 1995 (DE) ............................................. 195 24 347

(51) Int. Cl.[7] .................... G01N 33/68; G01N 33/574; G07K 14/025
(52) U.S. Cl. ................ 435/5; 435/7.1; 435/239; 436/518; 436/524; 436/527; 436/528; 436/531; 436/532; 436/815; 530/826
(58) Field of Search ................ 435/5, 7.1, 239; 436/518, 524, 527, 528, 531, 532, 815; 530/826

(56) References Cited

U.S. PATENT DOCUMENTS 4,748,109  5/1988  Baird .

FOREIGN PATENT DOCUMENTS 44 41 197  3/1996  (DE) .
0 256 321  2/1988  (EP) .
93 20844   10/1993 (WO) .
95 15497   6/1995  (WO) .

OTHER PUBLICATIONS

J. Clin. Microbiol. (1994), 32(9), 2216–20, Coden: JCMID-W;ISSN: 0095–1137, 1994, XP002019293, Sun, Yepng et al: "Comparison of peptide enzyme–linked immunosorbent assay and radioimmunoprecipitation assay with in vitro–translated proteins for detection of seruma antibodies to human papillomavirus type 16 E6 and E7 proteins".

Virology (1991), 182(2), 513–21 Coden: VIRLAX;ISSN: 0042–6822, 1991, XP002019292, Carter, Joseph J. et al: "Expression of human papillomavirus proteins in yeast *Saccharomyces cerevisiae*".

"Rapid Transformation of Cryoperserved Competent Schizosacharomyces pombe Cells", BioFeedback, vol. 15, No. 4, 1993, Michael Bröker.

"An Octomer of Histones in Chromatin and Free in Solution", Proc. Nat. Acad. Sci. USA, vol. 72, No. 7, pp. 2626–2630, Jul. 1975, Jean O. Thomas et al.

"A papillomavirus DNA from a cervical carcinoma and its prevalence in cancer biopsy samples from different geographic regions", Proc. Natl. Acad. Sci. USA, vol. 80, pp. 3812–3815, Matthias Dürst et al. (1983).

"Role of sulA and sulB in Filamentation by Lon Mutants of *Escherichia coli* K–12", Journal of Bacteriology, Oct. 1981, pp. 265–273, Susan Gottesman et al.

"Human Papillomavirus Type 18 E6*, E6, and E7 Protein 'synthesis in Cell–Free Translation Systems and Comparison of E6 and E7 in Vitro Translation Products to Proteins Immunoprecipitated from Human Epithelial Cells", Journal of Virology, Sep. 1991, pp. 5068–5072, Birgit Roggenbuck et al.

"Thiamine–repressible expression vectors pREP and pRIP for fission yeast", Gene, 123 (1993), pp. 127–130, Kinsey Maundrell.

"Association of Human Papillomavirus Types 16 and 18 Proteins with p54", Science, vol. 248, pp. 76–79, Bruce A. Werness et al. (1990).

*Primary Examiner*—Nathan M. Nutter
(74) *Attorney, Agent, or Firm*—Burns, Doane, Swecker & Mathis, L.L.P.

(57) ABSTRACT

The present invention relates to a method of detecting specific antibodies directed against HPV proteins in body fluids, comprising the following steps:

(I) incubating a native carrier material-bound HPV protein with body fluids, and (II) reacting specific antibodies (a) bound to the HPV protein
with labeled antibodies (b) directed against antibodies (a) or
with unlabeled antibodies (b) and the latter with labeled antibodies (c) directed against antibodies (b).

Furthermore, this invention concerns a kit usable for this purpose.

16 Claims, No Drawings

PROCESS FOR DETECTING SPECIFIC ANTIBODIES ACTING AGAINST HPV PROTEINS

This invention relates to a method of detecting specific antibodies directed against HPV proteins in body fluids. Furthermore, this invention concerns a kit usable for this purpose. Moreover, the invention deals with native HPV proteins suitable for carrying out the method according to the invention.

As is known, many people suffer from persistent infections caused by human papilloma viruses (hereinafter referred to as HPVs). As is also known, over 95% of all anogenital carcinomas, particularly of cervical carcinoma, and a considerable percentage of the carcinomas in the mouth/pharyngeal space are associated with persistent infections caused by HPVs.

In addition, there are indications that an uncontrolled expression of HPV genes, particularly genes of E6 and/or E7, is necessary for the formation of carcinomas in cells having a persistent infection caused by HPVs.

Therefore, the detection of such an expression could be a possibility serving for the early detection of HPV-associated carcinomas.

Thus, it is the object of the present invention to provide a method by which the uncontrolled expression of HPV genes, particularly of genes E6 and/or E7, can be detected.

According to the invention this is achieved by the subject matters defined in the claims.

Thus, the subject matter of the invention relates to a method of detecting specific antibodies directed against HPV proteins, which comprises the following steps:

(I) incubating a native, carrier material-bound HPV protein with body fluids, and (II) reacting specific antibodies (a) bound to the HPV protein
   with labeled antibodies (b) directed against antibodies (a), or
   with unlabeled antibodies (b) and the latter with labeled antibodies (c) directed against antibodies (b).

The method according to the invention is based on the applicant's finding that antibodies often exist in human beings who show uncontrolled expression of HPV genes, particularly of genes E6 and/or E7, which antibodies are directed against the expression products of these genes.

The above expression "HPV protein" comprises any protein of any HPV type. In particular, this expression relates to HPV-E6 and HPV-E7 proteins, more particularly of HPV 16 and HPV 18. The HPV protein may include a wild-type sequence. It may also have a sequence deviating therefrom, and the deviations may manifest themselves in the form of additions, deletions and/or substitutions of one or more amino acids. Furthermore, the HPV protein may be part of a fusion protein.

Common methods can be employed for the preparation of an HPV protein. It is favorable to insert a nucleic acid coding for an HPV protein, particularly a DNA, in an expression vector and employ the latter for the transfection of host cells and transformation of host cells, respectively.

A person skilled in the art knows a nucleic acid coding for an HPV protein (cf. Schwarz, E., 443–466 in "Papilloma Viruses and Human Diseases", (1987), Springer-Verlag). As regards HPV-E6 and HPV-E7 proteins, particularly of HPV 16 and HPV 18, he is also familiar with the following fact: EMBL data bank, AC K02718 for HPV 16; Swiss protein data bank P03126 for HPV 16-E6; Swiss protein data bank P03129 and Dürst, M. et al., Proc. Natl. Acad. Sci USA 60, (1983), 3812–3815 for HPV 16-E7; EMBL data bank, AC M20325 for HPV 18; Swiss protein data bank, P06463 for HPV 18-E6; Swiss protein data bank, P06788 for HPV 18-E7.

Furthermore, the person skilled in the art is familiar with expression vectors. In the case of an expression vector for $E.$ $coli$ these are e.g. pGEMEX, pUC derivatives, pGEX-2T, pET3b and pQE-8, the latter being preferred. For the expression in yeast these are e.g. pY100, Ycapdl and pREP-L20, the latter being preferred. For the expression in animal cells, e.g. PKCR, PEFBOS, cDM8 and pCEV4 have to be indicated, while particularly the baculovirus expression vector pAcSGHisNT-A is suitable for the expression in insect cells.

Moreover, the person skilled in the art knows host cells. Examples of such host cells comprise the $E.$ $coli$ strains HB101, DH1, x1776, JM101, JM109, BL21 and SG13009, the latter being preferred, the yeast strains saccharomyces cerevisiae and saccharomyces pombe, the latter strain being preferred, and the animal cells L, NIH 3T3, FM3A, CHO, COS, Vero and HeLa as well as the insect cells sf9.

Besides, the person skilled in the art is familiar with conditions of cultivating transformed host cells and transfected host cells, respectively. He also knows methods of isolating and purifying an expressed HPV protein.

In the method according to the invention, one or more HPV proteins, particularly a HPV-E6 and/or HPV-E7 protein, more particularly of HPV 16 and HPV 18, can be used simultaneously or one after the other. They are present in native form. Thus, all natural epitopes of specific antibodies, which are disposed on the HPV proteins, are provided. This optimizes the detection of specific antibodies over HPV proteins in denatured form. For obtaining an HPV protein in native form, such a protein can be folded back by common methods when it is present in denatured form. It is favorable to dissolve the denatured protein in a urea buffer, e.g. 10 mM Na phosphate, pH 7.4, 10% glycerin, 2 mM DTT, 8 M urea, feed it to a conventional hydroxylapatite column, e.g. HA Ultrogel, IBF Biotechnics, elute it with a conventional elution buffer of the above urea molarity, e.g. 150 mM NaPi, pH 7.8, 10% glycerin, 2 mM DTT, 1 M NaCl, 8 M urea, dialyze it against a common dialysis buffer of descending urea molarity, e.g. 50 mM Tris-HCl, pH 7.5, 0.1 mM ZnAc, 1 mM DTT, 50 mM NaCl, 4 M urea, feed it to a common anion exchanger, e.g. Q sepharose (Pharmacia), elute it with a conventional elution buffer of a urea molarity equal to the above dialysis urea buffer, e.g. 50 mM Tris-HCl, pH 7.5, 0.1 mM ZnAc, 1 mM DTT, 1 M NaCl, 4 M urea, subject it to a common collecting step, e.g. gel filtration, and dialyze it against a conventional dialysis buffer, e.g. 5 mM hepes, 5% glycerin, 1 mM DTT, 20 $\mu$M ZnAc.

As an alternative, it is favorable to dissolve the denatured protein in a urea buffer, e.g. 100 mM phosphate buffer, pH 8.0, 8 M urea, and subject it to step-wise dialysis against common dialysis buffers, e.g. 50 mM Mops/NaOH, pH 7.8, 500 mM NaCl, 20% glycerin, 5 mM DTT, 100 $\mu$M $ZnCl_2$. The dialysis buffers have descending urea molarities, e.g. 8 M, 3 M, 1 M and 0 M, respectively. The dialyses are carried out as usual, e.g. within 24 hours each. After the last dialysis, a folded-back HPV protein is obtained which is collected as usual, e.g. by gel filtration, particularly by Superdex 200 (Pharmacia). An HPV protein which was folded back as described above, also belongs to the subject matter of the present invention.

According to the invention an HPV protein is bound to a carrier material. Any material suitable for binding proteins, particularly microtiter plates, small tubes, microspheres and slides, can be used as such a carrier material. The attachment between HPV protein and carrier material may be effected according to common methods. It is favorable for the HPV protein to be present together with a tag polypeptide forming the C terminus, e.g. 11 amino acids, of SV40t antigen as fusion protein, so that it can be linked with the carrier material via a generally obtainable antibody directed against the tag polypeptide.

According to the invention an HPV protein linked with a carrier material is incubated with body fluids. These body fluids comprise all fluids that can be obtained from an animal body, particularly a mammal and more particularly a human being. The fluids comprise preferably serum, lymph, saliva, sputum, urine, stool, liquor, bile and gastrointestinal secretions. Furthermore, they also comprise fluids which can be isolated from solid tissues such as lungs, brain and bone marrow, smears and biopsies as well as tumors, e.g. anogenital carcinomas. The HPV protein can be incubated with body fluids according to common methods.

The above incubation serves for binding antibodies which are specific to an HPV protein. Such antibodies (hereinafter referred to as (a)) are then reacted with labeled antibodies (b) directed against antibodies (a) or with unlabeled antibodies (b) and the latter with labeled antibodies (c) directed against antibodies (b).

The labeling may be radioactive or non-radioactive. In the latter case, other common markers are used. Especially fluorescent dyes, such as fluorescein isothiocyanate, and enzymes such as alkaline phosphatase or peroxidase, are suitable. A biotin/streptavidine complex can be used as intensifier system. The markers are generally available. Antibodies (b) or (c) are conjugated according to the manufacturer's instructions. Previously labeled antibodies (b) and (c) are also generally available.

The selection of the suitable antibodies (b)—whether labeled or unlabeled—depends on the animal and animal species, respectively, from which the employed body fluid originates. For example, if a fluid from a human being is concerned, antibodies (b) used will be those directed against human immunoglobulin. Correspondingly, if antibodies (c) are used additionally, they will be selected with respect to the animal or the animal species from which antibodies (b) originate. The person skilled in the art is familiar with the selection of suitable antibodies and this selection can readily be made.

The conversion of bound antibodies (a) with labeled antibodies (b) and unlabeled antibodies (b) as well as then with labeled antibodies (c), respectively, can be made as usual. It is favorable to allow the conversion with antibodies (b) to take place in both alternatives at 37° C. within 1 h. After several wash steps, a substrate solution corresponding to the marker is added in the first alternative to develop the detection reaction. It is made in accordance with the manufacturer's instructions. In the second alternative, antibodies (c) are added after the wash steps. Their conversion and the development of the detection reaction are effected correspondingly.

The method according to the invention has a high degree of specificity. It is especially high when step (I) uses an HPV-tag fusion protein. Furthermore, the method according to the invention has a high degree of sensitivity. It is especially high when step (II) also uses antibodies (c). Moreover, it is often favorable to use in step (I) additionally one or more denatured HPV proteins and/or one or more fragments thereof. Thus, specific antibodies can be detected which are directed e.g. against degradation products of an HPV protein. The above statements made on the method according to the invention, particularly for attaching a native HPV protein to a carrier material and for incubating the protein with body fluids, here apply correspondingly.

According to the invention, a kit is also provided which is suited to carry out the above method. This kit contains preferably one or more native, carrier material-bound HPV proteins, optionally one or more denatured, carrier material-bound HPV proteins and/or fragments thereof, and labeled antibodies (b) according to claim 1, as well as conventional wash buffers and optionally a substrate corresponding to the labeling, or one or more native, carrier material-bound HPV proteins, optionally one or more denatured, carrier material-bound HPV proteins and/or fragments thereof and unlabeled antibodies (b) and labeled antibodies (c) according to claim 1 as well as conventional wash buffers and optionally a substrate corresponding to the labeling.

The above statements made on the method according to the invention apply here correspondingly.

By means of the present invention it is possible to detect an uncontrolled expression of HPV genes, particularly of genes E6 and/or E7. Thus, the invention is suited for the early detection of HPV-associated carcinomas.

The following examples explain the invention.

EXAMPLE 1

Preparation of an HPV 16-E7 protein and an HPV 16-E7 tag fusion protein (a) Preparation of an HPV 16-E7 protein The original DNA of HPV 16 was used as a basis (cf. Dürst M. et al., above). This DNA was used as template for a PCR method. The following primer pair was used: 5'-TTTGGATCCATGCATGGAGATACACCTACATTG-3' and 5'-TTTGTCGACTTATGGTTTCTGAGA-3'. PCR batch and conditions were standard.

The amplified DNA was cleaved by BamHI and SalI and inserted in the yeast shuttle vector pREP-L20 opened by BamHI and SalI. This vector corresponds to pREP3 (cf. Maundrell, K., Gene 123 (1993), 127–130), but contains the below "multiple cloning site":

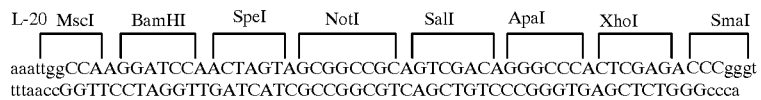

```
L-20 MscI    BamHI    SpeI    NotI    SalI    ApaI    XhoI    SmaI
aaattggCCAAGGATCCAACTAGTAGCGGCCGCAGTCGACAGGGCCCACTCGAGACCCgggt
tttaaccGGTTCCTAGGTTGATCATCGCCGGCGTCAGCTGTCCCGGGTGAGCTCTGGGccca
```

The expression plasmid pREP3-L20 HPV16-E7 was obtained. It was used for the transfection of schizosaccharomyces pombe LEU 1.32 (cf. Broker, M. Biotechniques, 6 (1993), 119). The transfected yeast cells were cultivated in a conventional "pombe min" medium in the presence of thiamine overnight. By this the "no message thiamine"

promoter of the above expression plasmid was suppressed. After washing off the thiamine and cultivation in thiamine-free medium, the promoter was switched on and the HPV 16-E7 gene was expressed. The HPV16-E7 protein was isolated after the mechanical breaking-open of the yeast cells.

(b) Preparation of an HPV 16-E7 tag fusion protein

The original DNA of HPV 16 was used as a basis (cf. Dürst, M. et al., above). This DNA was used as template for a PCR method. The following primer pair was used: 5'-TTTTCTAGAAGATCTATGCATGGAGATACACCT-3' and 5'-TTTGGATCCTGGTTTCTGAGAACA-3'. PCR batch and conditions were standard.

The amplified DNA was cleaved by BglII and BamHI and inserted in the bluescript vector pL441 opened by BglII and BamHI and coding for a tag polypeptide. The resulting DNA molecule was cleaved by XbaI and SalI and the HPV 16-E7 tag DNA was isolated. This DNA was inserted in the expression vector pREP-L20 opened by XbaI and SalI (see above). The expression plasmid pREP-L20 HPV 16-E7 tag was obtained. It was used for the transfection of schizosaccharomyces pombe Leu 1.32 (see above). The cultivation of the yeast cells and the expression of the HPV 16-E7 tag gene as well as the isolation of the HPV 16-E7 tag fusion protein were as described in 1(a).

EXAMPLE 2

Folding back of an HPV 16-E7 protein and an HPV 16-E7 fusion protein (a) Folding back of an HPV 16-E7 protein The HPV 16-E7 protein obtained in Example 1(a) was present in insoluble, denatured form. It was dissolved in a buffer, 25 mM Tris-HCl, pH 8.0, 10% glycerin, 2 mM DTT, 6 M guanidine hydrochloride, 50 mM NaF, 0.1 mM Na-o-yanadate. For its folding-back it was diluted 1:12 in a urea buffer, 10 mM Na phosphate, pH 7.4, 10% glycerin, 2 mM DTT, 8 M urea, and fed to a hydroxylapatite column (HA Ultrogel, IBF Biotechnics). The HPV protein was eluted with a urea elution buffer, 150 mM NaPi, pH 7.8, 10% glycerin, 2 mM DTT, 8 M urea, and dialyzed against a urea dialysis buffer, 50 mM Tris-HCl, pH 7.5, 0.1 mM ZnAc, 1 mM DTT, 50 mM NaCl, 4 M urea. The dialyzate was fed to an anion exchanger, Q-Sepharose (Pharmacia), and the HPV protein was eluted with a urea dialysis buffer, 50 mM Tris-HCl, pH 7.5, 0.1 mM ZnAc, 1 mM DTT, 1 M NaCl, 4 M urea. The eulate was subjected to a common gel filtration and then dialyzed against a dialysis buffer, 5 mM hepes, 5% glycerin, 1 mM DTT, 20 $\mu$M ZnAc. A native HPV 16-E7 protein was obtained.

(b) Folding back of an HPV 16-E7 tag fusion protein

The denatured HPV 16-E7 tag fusion protein obtained in Example 1(b) was folded back as described in Example 2(a). A native HPV 16-E7 tag fusion protein was obtained.

EXAMPLE 3

Detection of HPV-specific antibodies in sera of female patients suffering from cervical carcinoma (a) ELISA using an HPV 16-E7 protein For carrying out an ELISA, the HPV 16-E7 protein solution of Example 2(a) was diluted in a carbonate buffer, pH 9.6. For coating a 96-well plate, the wells were supplied with 100 ng of the HPV protein each and one well was supplied with carbonate buffer as empty control. Incubation at 4° C. overnight was followed by 6 short wash steps using PBS, 0.05% tween 20. Then, free binding sites of the polymeric carrier were blocked by one-hour incubation using an irrelevant protein, e.g. pig skin gelatin, BSA or casein, the latter being preferred, in PBS at 37° C. Sera of female patients suffering from cervical carcinoma and of control persons, in each case from Mexico, were incubated in PBS (1:50 dilution) at 37° C. on the plate for 1 hour. After another wash step using PBS, 0.05% tween 20, a generally available peroxidase-coupled goat anti-human antibody (Zymed Laboratories, CA, U.S.A.; dilution according to the manufacturer's instructions) was added. One hour of incubation at 37° C. was followed by another wash step and thereafter by the peroxidase detection reaction using TMB developer solution (50 mM sodium acetate, 0.4 mM 3,3',5, 5'-tetramethylbenzidine dihydrochloride, 4,4 mM $H_2O_2$) at room temperature within 30 minutes. Having stopped the reaction by 1 M sulfuric acid, the color intensity was determined photometrically at 450 nm.

It showed that HPV-specific antibodies can be detected in sera of female patients suffering from cervical carcinoma by an HPV 16-E7 protein.

(b) ELISA using an HPV 16-E7 tag protein

For carrying out an ELISA with the HPV 16-E7 tag protein of Example 2(b), a 96-well plate was coated with 200 ng per hole of the generally obtainable monoclonal mouse antibody Mab tag (KT3) directed against the tag polypeptide. For this purpose, the plate was incubated with the antibody dissolved in the above carbonate buffer at 4° C. overnight. After six short wash steps using PBS, 0.05% tween 20, the HPV 16-E7 tag protein dissolved in the above carbonate buffer was added in an amount of 100 ng per well. The further steps were carried out as described in Example 3(a).

It showed that HPV-specific antibodies can be detected in sera of female patients suffering from cervical carcinoma by an HPV 16-E7 tag protein.

Both detections of Example 3(a) and (b) were more specific than a comparative ELISA which used an HPV 16-E7 fragment, i.e. no native protein. In this connection, the specificity of the detection of 3(b) was even greater than that of the detection of 3(a). In 3(a), 2 positive examples were obtained among 64 control values, whereas in 3(b) all of these control values were negative. Furthermore, 28 of 73 sera from the female patients suffering from cervical carcinoma could be detected as HPV-specific in 3(b), whereas in 3(a) it was only 20.

EXAMPLE 4

Preparation and purification of HPV 16(18) E6 (E7) proteins (a) Preparation and purification of an HPV 16-E6 protein The plasmid pGem-2/16E6 was used as a basis. It contains a DNA coding for the E6 protein of HPV 16 (cf. Werness, B. A. et al., Science, Vol. 248, (1990), 76–79). This DNA was used as a template for a PCR method. The following primer pair was used: 5'-CAGGGATCCGATGACGATGACAAAATGTTTCAG-GACCCACAGG-3' and 5'-GGGAAG-CTTATTACAGCTGGGTTTCTCTAC-3'. The PCR batch and the PCR conditions, respectively, were as follows:

PCR batch template DNA: 1 $\mu$l=1 ng

Pfu polymerase 10×buffer: 10 $\mu$l=1×

DMSO: 10 $\mu$l=10% dNTPs: 1 $\mu$l=200 $\mu$M each oligonucleotides, 1.5 $\mu$l each: 3 $\mu$l 150 ng each $H_2O$ bidistilled: ad 99 $\mu$l PCR conditions
92° C. −5 min
addition of 1 μl Pfu polymerase (Stratagene)=2.5 units
addition of paraffin
PCR
92° C. 1 min
58° C. 1 min 1 cycle
72° C. 10 min
92° C. 1 min
58° C. 1 min 39 cycles
72° C. 2 min
72° C. 10 min 1 cycle The amplified DNA was cleaved by BamHI and HindIII and inserted in the expression vector pQE-8 (Qiagen) opened by BamHI and HindIII. The expression plasmid pQ/16/E6 was obtained. It codes for a fusion protein consisting of 6 histidine residues and an enterokinase restriction site (N terminus partner) as well as the E6 protein of HPV 16 (C terminus partner). pQ/16/E6 was used for the transformation of E. coli SG 13009 (cf. Gottesman, S. et al., J. Bacteriol. 148, (1981), 265–273). The bacteria were cultivated in an LB medium with 100 μg/ml ampicillin and 25 μg/ml kanamycin and induced with 60 μM isopropyl-β-D-thiogalactopyranoside (IPTG) for 4 h. Lysis of the bacteria was achieved by adding 6 M guanidine hydrochloride. Then, a chromatography (Ni-NTA resin) was carried out with the lyzate in the presence of 8 M urea in accordance with the instructions from the manufacturer (Qiagen) of the chromatography material. The bound fusion protein was eluted in a buffer having pH 3.5. After its neutralization, the fusion protein was subjected to an 18% SDS polyacrylamide gel electrophoresis and dyed using coomassie blue (cf. Thomas, J. O. and Kornberg, R. D., J. Mol. Biol. 149 (1975), 709–733).

A pure HPV16-E6 fusion protein (molecular weight about 18 kD) was obtained. It was present in denatured form.

(b) Preparation and purification of HPV 16-E7 and HPV 18-E6 (E7) proteins

HPV 16-E7 and HPV 18-E6 (E7) proteins were prepared and purified as described in 4(a). The following deviations were carried out:

For the preparation of HPV 16-E7, the plasmid pWV 2916 was used as a basis. It contains a DNA coding for HPV 16 (cf. Dürst, M. et al., Proc. Natl. Acad. Sci, U.S.A., Vol. 60, (1983), 3812–3815). The following primer pair was used for the PCR method:
5'-CAGGGATCCATGCATGGAGATACACCTAC-3' and
5'-GGGAAGCTTATTATGGTTTCTGAGAACAGATG-3'.

After cloning the amplified DNA in pQE-8 (pQ/16/E7), with the DNA failing to have an enterokinase restriction site, and expressing it in SG 13009 as well as purifying it, a pure HPV 16-E7 fusion protein (molecular weight about 12 kD) was obtained. It was present in denatured form.

For the preparation of HPV 18-E6, the plasmid pGem1/18 E6 was used as a basis. It contains a DNA coding for the HPV 18-E6 protein (cf. Werness, B. A. et al., above). The following primer pair was used for the PCR method:
5'-CAGAGATCTGATGACGATGACAAAATGGCGCG-CTTTGAGGATC-3' and 5'-GGGAAGCTTATTATACTT-GTGTTTCTCTGCG-3'.

After cloning in pQE-8 (pQ/18/E6) and expression in SG 13009, a pure HPV18-E6 fusion protein (molecular weight about 19 kD) was obtained. It was present in denatured form.

For the preparation of HPV 18-E7, the plasmid pGEM 3/91 was used as a basis. It contains a DNA coding for HPV 18 (cf. Roggenbuck, B. et al., J. Virol., Vol. 65, (1991), 5068–5072). The following primer pair was used for the PCR method:
5'-CAGGGATCCATGCATGGACCTAAGGCAAC-3' and
5'-GGGAAGCTTATTACTGCTGGGATGCACACC-3'.

After cloning the amplified DNA in pQE-8 (pQ/18/E7), with the DNA failing to contain an enterokinase restriction site, and expressing it in SG 13009, a pure HPV 18-E7 fusion protein (molecular weight about 13 kD) was obtained. It was present in denatured form.

EXAMPLE 5

Folding back of denatured HPV 16(18)-E6(E7) proteins (a) Folding back of an HPV 16-E6 protein The HPV 16-E6 protein obtained in Example 4(a) was dissolved in a urea buffer (100 mM phosphate buffer, 8 M urea, pH 8.0) and subjected to step-wise dialysis. The dialysis buffers included 50 mM Mops/NaOH, pH 7.8, 500 mM NaCl, 20% glycerin, 5 mM DTT, 100 μM $ZnCl_2$. In addition, they included 8 M, 3 M, 1 M and 0 M, respectively, of urea. The individual dialyses were carried out in each case within 24 hours. Thereafter, gel filtration was carried out by Superdex 200 (Pharmacia).

A HPV 16-E6 protein was obtained in native form.

(b) Folding back of HPV 16-E7 and HP 18-E6 (E7) proteins

The HPV 16-E7, HPV 18-E6 (E7) proteins obtained in Example 4(b), were folded back as described in 5(a). Corresponding HPV proteins were obtained in native form.

EXAMPLE 6

Detection of HPV-E6 and HPV-E7-specific antibodies in patients' sera

For carrying out an ELISA, HPV 16-E6 and HPV 16-E7 proteins of Example 5 were taken up in buffers (0.1 M $NaH_2PO_4$, pH 8.0). For coating a 96-well plate, each well was supplied by pipetting with 100 μl including 20 ng and 8 ng, respectively, of the HPV proteins, and one well was supplied by pipetting with 1% BSA as empty control. After incubation at 4° C. overnight, 4 short wash steps, using PBS, 0.05% tween 20, followed in each case at intervals of 5 min. Thereafter, the free binding sites of the polymeric carrier were blocked by overnight incubation using 1% BSA in PBS, 0.05% tween 20, at 4° C. A serum to betested, which was obtained from a female patient suffering from cervical carcinoma, was incubated on the plate at 1:100 dilution (PBS, 1% BSA, 0.05% tween 20) at 37° C. for 1 hour ("chessboard titration"). After 4 short wash steps using PBS, 0.05% tween 20, at intervals of 5 min, a generally obtainable peroxidase-coupled goat anti-human antibody (dilution in accordance with the manufacturer's instructions) was added. Incubation at 37° C. for 30 minutes was followed by 4 wash steps again, as outlined above, and thereafter by the peroxidase detection reaction using TMB developer solution (50 mM sodium acetate, 0.4 mM 3,3,5,5'-tetramethylbenzidine dihydrochloride, 4.4 mM $H_2O_2$) at room temperature within 30 minutes. After stopping the reaction using 2 M HCl, the color intensity was determined photometrically at 450 nm. Absorption values of over two times the BSA control were considered to be a positive reaction.

It showed that HPV-E6- and HPV-E7-specific antibodies can be detected in the serum of a female patient suffering from cervical carcinoma.

What is claimed is:

1. A method of detecting specific antibodies directed against HPV proteins in body fluids, comprising the following steps:

(I) incubating a native, carrier material-bound HPV protein with body fluids, and (II) reacting specific antibodies (a) bound to the HPV protein
with labeled antibodies (b) directed against antibodies (a) or
with unlabeled antibodies (b) and the latter with labeled antibodies (c) directed against antibodies (b).

2. The method according to claim 1, wherein a HPV-tag fusion protein is used in step (I).

3. The method according to claim 1, wherein, in addition, one or more denatured, carrier material-bound HPV proteins and/or fragments thereof are used in step (I).

4. The method according to claim 1, wherein the HPV protein is an HPV-E6 or HPV-E7 protein.

5. The method according to claim 1, wherein the HPV protein originates from HPV 16 or HPV 18.

6. The method according to claim 1, wherein several native HPV proteins are used in step (I).

7. The method according to claim 1, wherein the native HPV protein is obtained by folding back a corresponding denatured protein.

8. The method according to claim 7, wherein the folding-back of the denatured HPV protein comprises a solution of this protein in a urea buffer and a dialysis of the dissolved protein in common buffers with descending molarities of urea and a gel filtration of the dialyzed protein.

9. The method according to claim 7, wherein the folding-back of the denatured HPV protein comprises dissolving the protein in a common urea buffer, applying it to a common hydroxylapatite column, eluting it using a common elution buffer having the above area molarity, dializing it against common dialysis buffers of descending urea molarity, applying it to a common anion exchanger, eluting it by means of a common elution buffer having a urea molarity equal to the above dialysis buffers, carrying out gel filtration, and dialyzing against a common dialysis buffer.

10. The method according to claim 1, wherein the body fluids comprise serum, lymph, saliva, sputum, urine, stool, liquor, bile, gastrointestinal secretions and fluids obtained from solid tissues and tumors.

11. The method according to claim 1, wherein the carrier material comprises microtiter plates, small tubes, microspheres and slides.

12. The method according to claim 1, wherein antibodies (b) of the first alternative and antibodies (c) of the second alternative are labeled with an enzyme.

13. The method according to claim 1, wherein antibodies (b) of the first alternative and antibodies (c) of the second alternative are labeled with a fluorescent dye.

14. The method according to claim 1, wherein antibodies (b) of the first alternative and antibodies (c) of the second alternative are labeled radioactively.

15. A kit comprising
one or more native, carrier material-bound HPV proteins, optionally one or more denatured, carrier material-bound HPV proteins and/or fragments thereof, and labeled antibodies (b) according to claim 1 and common wash buffers and optionally a substrate corresponding to the labeling, or
one or more native, carrier material-bound HPV proteins, optionally one or more denatured, carrier material-bound HPV proteins and/or fragments thereof, and unlabeled antibodies (b) and labeled antibodies (c) according to claim 1 and common wash buffers and optionally a substrate corresponding to the labeling.

16. Native HPV proteins, obtained by the method according to claim 7.

* * * * *